(12) United States Patent
Ten Hoeve et al.

(10) Patent No.: US 7,402,707 B2
(45) Date of Patent: Jul. 22, 2008

(54) METHOD OF PREPARATION OF A PRECURSOR OLIGOCENE

(75) Inventors: Wolter Ten Hoeve, Assen (NL); Bart-Hendrik Huisman, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 376 days.

(21) Appl. No.: 10/548,938

(22) PCT Filed: Mar. 17, 2004

(86) PCT No.: PCT/IB2004/050264

§ 371 (c)(1), (2), (4) Date: Sep. 12, 2005

(87) PCT Pub. No.: WO2004/083160

PCT Pub. Date: Sep. 30, 2004

(65) Prior Publication Data

US 2006/0166409 A1  Jul. 27, 2006

(30) Foreign Application Priority Data

Mar. 18, 2003 (EP) .................................. 03100684

(51) Int. Cl.
C07C 49/00 (2006.01)
C07C 43/30 (2006.01)
C07C 43/20 (2006.01)
C07C 15/02 (2006.01)

(52) U.S. Cl. ................... 568/377; 568/591; 568/659; 585/400

(58) Field of Classification Search .............. None
See application file for complete search history.

(56) References Cited

U.S. PATENT DOCUMENTS 6,855,949 B2  2/2005  De Leeuw et al.

FOREIGN PATENT DOCUMENTS

WO  WO03030278 A2  4/2003
WO  WO03079400 A2  9/2003

OTHER PUBLICATIONS

Peter T Herwig, et al: Soluble Pentacene Precursor: Systhesis, Solid-State Conversion into Pentcene and Application in a Field-Effect Transistor, vol. 11, No. 6, 1999, pp. 480-483, XP-000829967.

*Primary Examiner*—Sikarl A Witherspoon

(57) ABSTRACT

The synthesis of a precursor oligocene, particularly pentacene, is a two-step process. In the first step the Diels-Alder adduct of the a,b-dihydro-a,b-etheno-oligocene with a 1,1-dialkoxy-cyclopentadiene is formed. In the second step this Diels-Alder adduct is converted into the precursor oligocene, in that first the corresponding keto-compound is formed, which may be eliminated thereafter. The resulting precursor oligocene can be converted to the oligocene with a heat treatment, particularly after providing a solution hereof on a substrate. It is suitable for use as semiconductor material in a thin-film transistor. Formula (I).

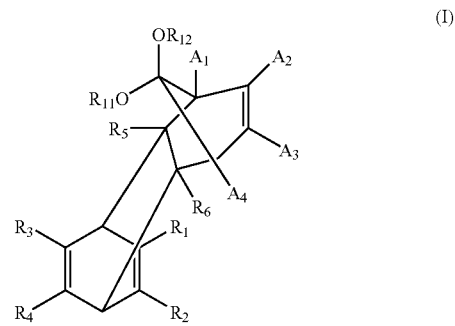

9 Claims, 2 Drawing Sheets

METHOD OF PREPARATION OF A PRECURSOR OLIGOCENE

Figure 1:
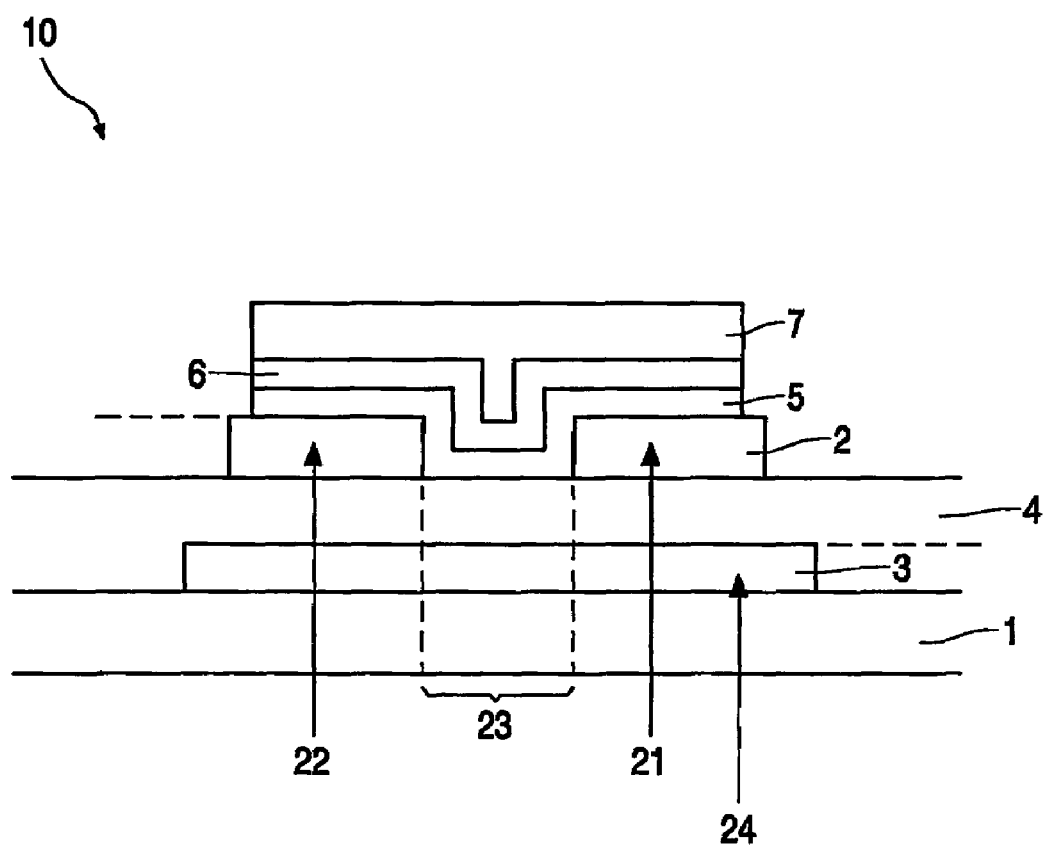

The invention relates to a method of preparation of a precursor oligocene compound,

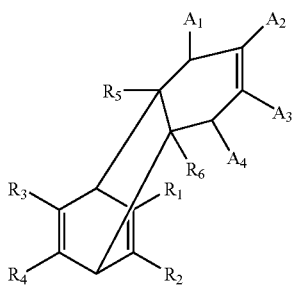

in which $R_1, R_2, =$ 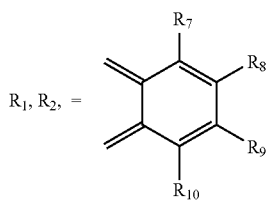

$R_3$, $R_4$ are the same as $R_1$, $R_2$ or H, alkyl, aryl, alkoxy, aryloxy or halogen;

$R_5$, $R_6$ are H, $C_1$-$C_4$-alkyl, CN, $C_1$-$C_4$-alkoxy or halogen and may be the same or different;

$R_7$, $R_8$, $R_9$, $R_{10}$ are H, alkyl, aryl, halogen or alkoxy, and may be the same or different, and $R_7$ and $R_8$, $R_8$ and $R_9$, $R_9$ and $R_{10}$ may be in combination

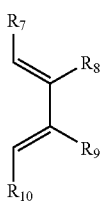

$A_1$, $A_2$, $A_3$, $A_4$, are H or an electron withdrawing group such as Cl, Br, I, F, H, CN, $OCH_3$, $CF_3$, and may be the same or different.

The invention also relates to precursor oligocene compounds, and to a method of preparation of an oligocene from the precursor Oligocene compound.

The invention further relates to a method of manufacturing an electronic device comprising a thin-film transistor provided with a layer of an organic semiconductor material, wherein the layer comprises an Oligocene as the semiconductor material, and to an electronic device obtainable therewith.

Such a method of preparation of a precursor Oligocene compound is known from Herwig and Müllen, Adv.Mater., 11(1999), 480-483. In the known method the precursor oligocene compound is a precursor pentacene. It is prepared by reacting the 6,13-dihydro-6,13-etheno-pentacene with 2,3,4,5-tetrachloro-thiophenedioxide. This results in 6,13-dihydro-6,13-(2,3,4,5-tetrachloro-2,4-cyclohexadieno)pentacene, as the precursor compound. A dispersion or solution or this compound can be applied onto a substrate and thereafter be converted to pentacene by heating to 200° C.

It is a disadvantage of the known method of preparation, that the Diels-Alder reaction is performed at extremely high pressure (6 kbar) to obtain a reasonable yield. Such a high pressure is not reasonably applicable at larger scale synthesis.

It is therefore an object of the invention to provide a method of preparation of the kind mentioned in the opening paragraph, in which the Diels-Alder reaction can be performed at lower pressures.

This object is achieved in that the method comprises the steps of:

reacting an dihydro-etheno-oligocene with a 1,1-($R_{11}O$)($R_{12}O$)— cyclopentadiene to form a Diels-Alder adduct, wherein the $R_{11}$, $R_{12}$ H, $C_1$-$C_8$-alkyl, aryl, aralkyl, alkaryl and $R^1$ and $R^2$ may be different or equal to each other, and may form together a ringshaped chain, and converting the adduct with an electrophilic or oxidizing agent to obtain the precursor oligocene compound.

Surprisingly, the use of the 1,1-($R_{11}O$)($R_{12}O$)-cyclopentadiene results in a stable intermediate, which is an acetal. This acetal can be reacted in a subsequent step under relatively mild conditions to the known precursor oligocene. In this step the acetal is first converted into the corresponding keton. This keton can be obtained and can be used as a precursor compound itself as well. The electrophilic or oxidizing agent can be any agent as known to the skilled art, which is at least capable of converting an acetal into a keton and is an acid by preference.

The Diels-Alder reaction in the method of the invention needs not to be performed at such high pressures as the prior art method. The reason for the high pressure in the prior art method was that the formed precursor converts to oligocene. The oligocene so formed will readily react with tetrachlorothiophenedioxide to give a by-product, that is difficult to remove. By performing the reaction at very high pressures, this further reaction is suppressed. As the intermediate in the present method is stable, neither the precursor oligocene, nor the oligocene, nor the by-product are formed during the Diels-Alder reaction.

The oligocene is by preference pentacene. However, it may be for instance heptacene, nonacene or the like. The pentacene as conventionally used has a linear chain; however non-linear configurations, such as those obtainable with the starting compound dihydro-dietheno-oligocene as shown below, are not excluded. The pentacene may be provided with any suitable side chains, including alky- and alkoxygroups, aryl-, aralkyl, alkaryl, aryloxy and the like.

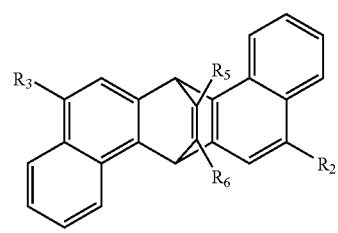

Particularly preferred are one or more (particularly 1-3) alkyl chains with functionalized end groups. Such end groups are for instances acrylates, esters, thiols, which are suitable to react with other groups or to adhere to a substrate surface.

Reactive end groups are interesting so as to form a polymer or a polymer network comprising semiconductor elements with a limited conjugation length, as described in the non-prepublished application EP02076053.4 (PHNL020257). Such polymers and polymer networks are advantageous in that they are stable in air and light, can be aligned if the alkylchains are sufficiently long (for instance hexyl), and that they can be patterned without the need to apply a photoresist on top of the layer.

For reasons of simplicity, the advantages and embodiments will be discussed with reference to pentacene. However, there is no reason that these would apply to pentacene only.

It is an advantage of the method of the invention that it can be performed at larger scales; in first experiments, a scale of a few hundred grams was tried successfully. There is no reason that the scale cannot be increased any further, although such a scale is sufficient for the industrial application of pentacene as an organic semiconductor material.

It is a further advantage that the yield of the method of the invention is much higher. A yield of about 75% was obtained for the Diels-Alder reaction and the subsequent conversion to the precursor pentacene.

It is another advantage, that the improved synthesis does not have a negative impact on the characteristics of a transistor with the pentacene as semiconductor material. The mobility obtained with the pentacene obtained with the prior art method and the pentacene obtained with the method of the invention is identical.

The precursor oligocene compound prepared in the invention is pentacene by preference. Pentacene turns out to have very good semiconductor properties and the precursor is reasonably processable; it is neither too viscous, nor is the conversion temperature of the precursor to pentacene too high, and it can be dissolved in standard solvents. The latter is the case in particular, if a carrier material, such as polystyrene, polyethylene or polyacrylaat, is added to the pentacene precursor. This is further described in the non-prepublished application IB02/0394 (PHNL010691).

The precursor group is preferably present at the ring-shaped part in the middle of the oligocene. In the case of pentacene, this is the third part, and the positions of the etheno-group or the Diels-Alder adduct, is conventionally indicated as the 6,13-positions.

The Diels-Alder reaction is preferably carried out with a halogenated 1,1-dialkoxycyclopentadiene. The cyclopentadiene is preferably tetrasubstituted, and the preferred halogenes are chloro and bromo. It is not necessary that all substitutions are the same halogen, although 2,3,4,5-tetrachloro-1,1-dialkoxycyclopentadiene is preferred.

The alkoxygroups $R_{11}O$, $R_{12}O$ are preferably chosen from hydroxy, methoxy, ethoxy, 1-propoxy, 2-propoxy, 1-n-butoxy, 2-n-butoxy, isopropoxy, t-butoxy, and all variants of pentoxy, as well as benzyloxy, toluoxy etc. The groups may be different or the same. The groups may further be cyclic, e.g. O—$R_{11}$—$R_{12}$—O. Particularly, if one group is larger, it is preferred that the other is smaller, so as to avoid steric hindrance. Particularly preferred is the 1,1-dimethoxy-cyclopentadiene, and most preferred is the 2,3,4,5-tetrachloro-1,1-dimethoxy-cyclopentadiene. This compound functions excellent in the reaction and is commercially available.

In a suitable embodiment, the 6,13-dihydro-6,13-etheno-pentacene is obtained by:
conversion of bicyclo[2.2.2]oct-2-ene-dianhydride into 5,6,7,8-tetramethylenebicyclo[2.2.2]oct-2-ene; and
conversion of the tetramethylene-bicyclo-octene with a 1,2-dihalogenobenzene and subsequent reduction.

This synthesis has the advantage that it is simplified in comparison with the prior art synthesis. Furthermore, the synthesis was performed at a kilogramme-scale and a good yield resulted. An overall yield of about 35% has been realized, with a yield of about 75% for the first step. Particularly, the first step is simplified in that another starting material has been chosen. This anhydride can be converted easily and with good yield in the corresponding ester, and particularly in the exo-endo-isomer. This exo-endo isomer is subsequently reduced to a tetrol. Thereafter the hydroxylgroups are substituted by chloridegroups, which are eliminated to give the tetramethylene-compound. Evidently, the yield may be further optimized.

The precursor oligocenes obtained in the method of the invention may be further converted into alternative precursors. This may be realized in that first precursors are converted into pentacene. Thereafter, the pentacene may be converted into the alternative precursor, for instance with a N-sulfinylamide such as known from Afzali, *J.Am.Chem. Soc.*, 124(2002), 8812.

The stable intermediates of the method of the invention are new compounds. Particularly the intermediate with the keto-bridge is advantageous, in that it can be used in itself as a precursor.

The precursor oligocenes can be converted into the desired oligocenes at elevated temperatures. Particularly such temperature is in the range of 100 to 230° C., which is further dependent on the chosen oligocene as well as the specific leaving group. The conversion may take place after that a solution of the precursor has been provided on a substrate.

Suitably, the solution comprises a carrier material. This carrier material simplifies the coating procedure. Besides, it provides a layer with a good mechanical stability, onto which other layers may be provided by spincoating. This further layer may include a photoresist, with which the Oligocene layer can be structured into a desired pattern. In order to prevent degradation of the transistor characteristics, it is preferred to apply a protective layer in between of the pentacene layer and the photoresist.

The pentacene-layer obtained is different from the pentacene-layers obtained according to the prior art. Particularly, the difference resides herein that the layer does not contain any pentacene-thiophenedioxide contamination, as is the case with the layers obtainable with the known method of preparation of the precursor pentacene.

The oligocene obtainable in according with the invention can be used as active constituent of an active layer in any semiconductor element, such as light-emitting diodes, photovoltaic cells and particularly field-effect transistors. The field-effect transistors are generally processed on an insulating substrate, and are also known as thin-film transistors in view of the thin-film active layer. The field-effect transistors may have electrodes of any metal, any oxidic conductor, such as indium-tin-oxide (ITO), and any polymeric conductor, such as a complex of poly(3,4-ethylenedioxy)thiophene and a polyacid. The field-effect transistors can be flexible and may be used in a flexible display, with an electro-optical layer of a liquid-crystalline or a electrophoretic material. Such display may be addressed actively or passively. Alternatively the field-effect transistors can be integrated in a integrated circuit, for instance for use in an identification label or security paper.

Figure 2:
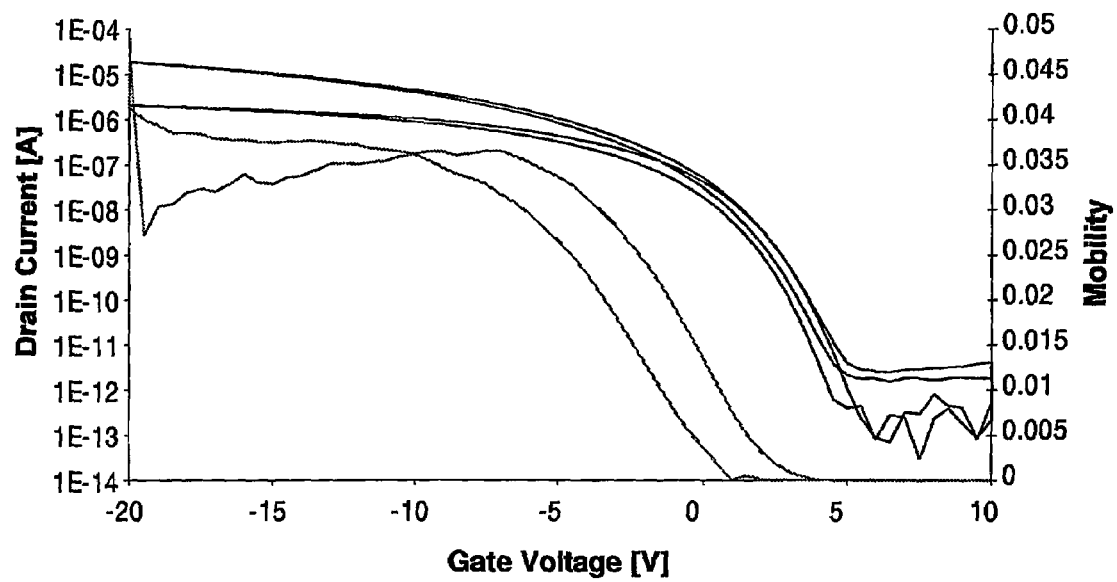
Figure 3:
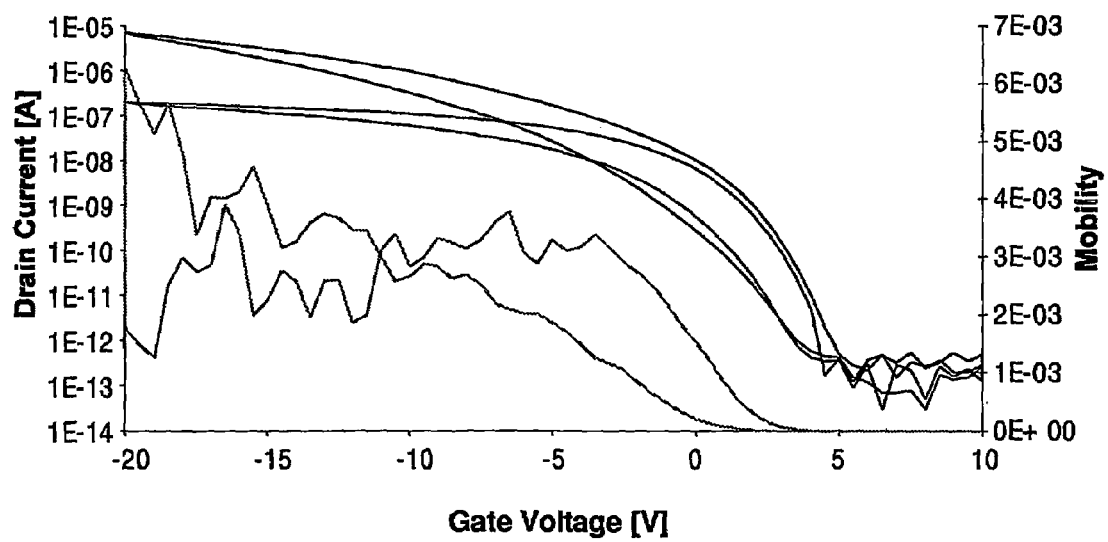

These and other aspects of the invention will be further elucidated with reference to the Figures, in which:

FIG. 1 shows a diagrammatical cross-sectional view of a field-effect transistor; and FIGS. 2 and 3 show graphs of the transistor characteristics obtained with the pentacene according to the invention FIG. 1 shows an thin-film transistor. It is provided with an electrically insulating substrate 1 with hereon a source electrode 21, a drain electrode 22, which electrodes are mutually separated through a channel 23 and are defined in a first electrode layer of electrically conductive material 2. A second electrode layer 3 of electrically conductive material is present at this side of the substrate 1 as well. A gate electrode 24 has been defined in this second electrode layer 3. A perpendicular projection of this gate electrode 24 on the first electrode layer 2 shows a substantial overlap with the channel 23. Furthermore, an intermediate layer 4 of dielectric material and an active layer 5 comprising a semiconductor material are present.

Said layers 2,3,4 and 5 are present on the substrate 1 in the order of second electrode layer 3, intermediate layer 4, first electrode layer 2 and active layer 5. A—non-shown—planarisation layer of polyvinylalcohol is present on the substrate 1 for planarazation. The second electrode layer 3 comprises Au and has been patterned photolithographically in conventional manner with a photosensitive resist material. A non-shown monolayer of $CH_3-(CH_2)_{15}-SH$ may be applied between the second electrode layer 3 and the intermediate layer 4 to prevent the existence of pinholes in the intermediate layer 4. The intermediate layer 4 comprises an organic dielectric that can be structured photochemically, such as for instance benzocyclobutene, polyimide, polyvinylfenol or a photoresist, and in this case the commercially available photoresist material HPR504. The first electrode layer comprises gold in this case and is provided with sputtering and in conventional manner structured photolithographically. The active layer 5 comprising pentacene and polystyrene (99 to 1% by weight), wherein the polystyrene acts as carrier material. The pentacene was converted from the precursor pentacene as prepared in according with the invention after application as active layer on the substrate. The conversion took place at 200° C. during 10 seconds which leads to full conversion. On the active layer 5 a protective layer 6 of electrically insulating material is present, as well as a photoresist 7. The layers 5, 6 and 7 form a stack and are provided with one and the same pattern. If intended as a display, an electro-optical layer can be provided on this stack, preferably after that a planarisation layer has been applied.

In order to test the pentacene as prepared in the invention tests were done with a test substrate, being a silicon substrate with a highly doped area acting as gate electrode, an intermediate layer of silicon dioxide and source and drain electrodes of Au. The results are shown in FIG. 2 and FIG. 3. FIG. 2 shows results for the pentacene that was converted from the precursor pentacene with the 2,3,4,5,-tetrachlorocyclohexadienylene as side group according to the invention. FIG. 3 shows results for the pentacene that was converted from the precursor pentacene with the 2,4-methylketon-2,3,4,5,-tetra-chlorocyclohexadienylene as side group. Results shown are the mobility (lines at the left) and drain current (line at the right) The observed mobility in the latter case is somewhat lower, which is however an effect of non-optimization. It is more important that the transistor characteristics obtained with the synthesis of the invention are at least as good as those of the prior art.

The precursor pentacene according to the invention was obtained as follows:

Full synthetic pathway for the synthesis of precursor pentacene 1 starting form commercially available materials.

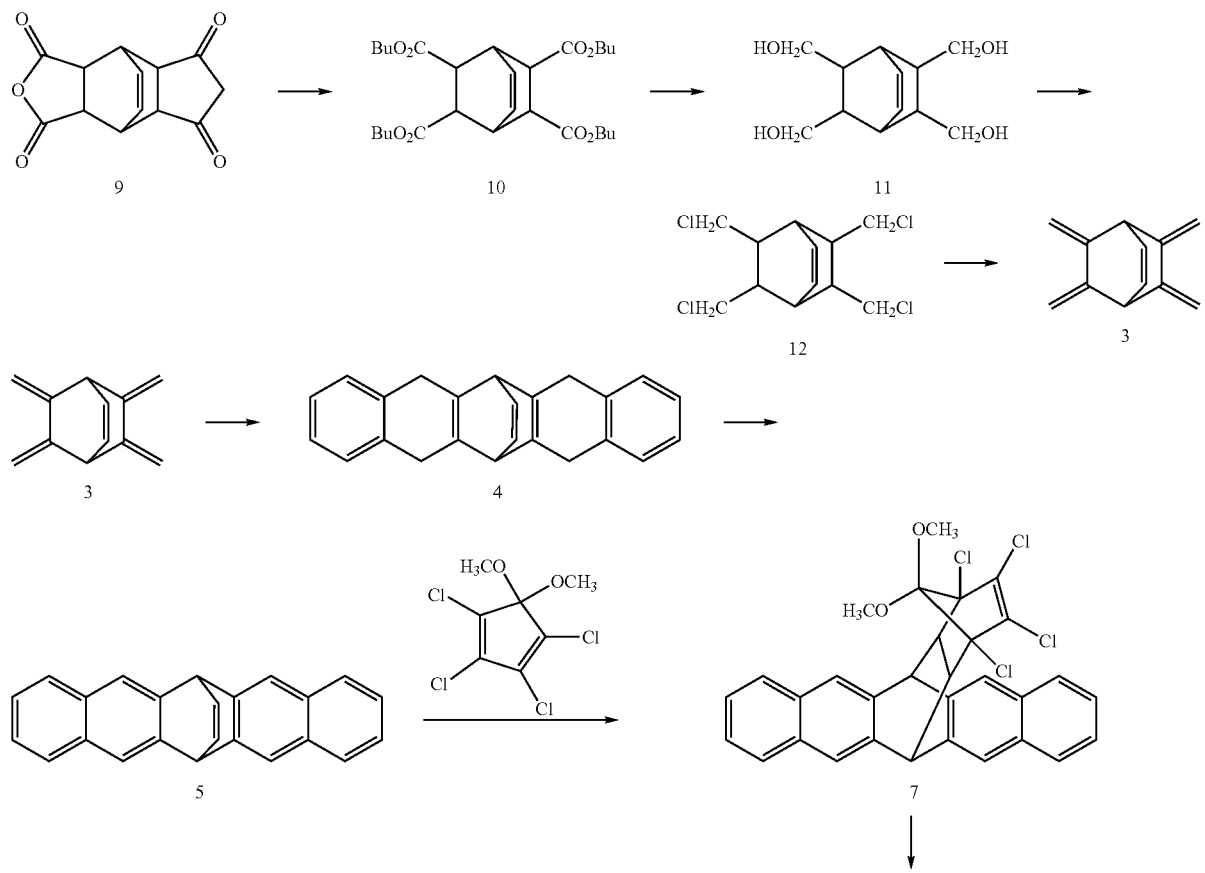

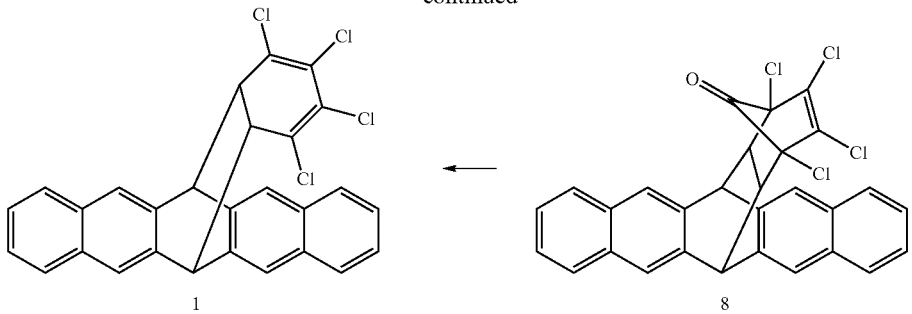

Experimental for Full Synthesis of Precursor Pentacene:

5-eno, 6-endo, 7-exo, 8-endo-bicyclo[2.2.2]oct-2-ene5,6,7,8-tetracarbonylic acid, tetrabutyl ester (10)

A mechanically stirred mixture of the anhydride 9 (1.00 kg, 4.03 mol), 1.7 L n-butanol (18.6 mol), 500 mL toluene, and 3.2 g p-toluenesulfonic acid is heated under reflux for 22 h with azeotropic removal of water (136.5 g collected). NMR indicates the presence of the all-exo isomer. After cooling a solution of sodium hydride (16.0 g, 55% in oil, 0.37 mol) in 70 mL n-butanol is added. The mixture is heated at 125-130° C. for 6 h. Until completion of the reaction the mixture is repeatedly cooled somewhat and additional sodium hydride in batches of 6.0 g (55% in oil) is added slowly, followed by heating for several hours. The mixture is rotary evaporated and the liquid residue is used as such in the next step $^1$H NMR of the all-exo isomer (CDCl$_3$): δ 0.8-1.7 (m, 28H), 3.0 (s, 4H), 3.35 (bs, 2H), 4.0 (m, 8H), 6.4 (bs, 2H). $^1$H NMR of the exo-endo isomer (CDCl$_3$): δ 0.8-1.7 (m, 28H), 2.8-3.3 (m, 4H), 3.5 (m, 2H), 4.0 (m, 8H), 6.35 (m, 2H).

5-exo, 6-endo, 7-exo, 8-endo-5,6,7,8-tetra(hydroxymethyl)-bicyclo[2.2.2]oct-2-ene (11)

The exo-endo isomer 10 obtained above is reduced with 464.3 g lithium aluminum hydride (12.22 mol) and 7.9 L THF, as follows: The ester, dissolved in some THF, is added over a period of 5 h to lithium aluminum hydride in THF, towards the end of the addition a very thick, barely stirrable suspension results. After stirring for another 30 minutes, the mixture is allowed to cool to RT and is then quenched by the slow addition of 200 g potassium hydroxide in 300 mL water The suspension is filtered and the solids are washed with THF. he dried solid is heated with 5.5 L methanol to near boiling. The warm suspension is filtered and the filtrate is neutralized with hydrochloric acid. Filtration and rotary evaporation gives the crude tetrol. A total of 1079 g of crude tetrol is. $^1$H NMR (D$_2$O): δ 1.0 (m, 2H), 1.35 (m, 2H), 2.5 (bs, 2H), 3.0-3.6 (m, 8H), 6.2 (bs, 2H).

5-exo, 6-endo, 7-exo, 8-endo-5,6,7,8-tetra(chloromethyl)-bicyclo[2.2.2]oct-2-ene (12)

To a mixture of the tetrol obtained above, 600 mL pyridine and 100 mL toluene there is added thionyl chloride (660 mL, 8.90 mol). The temperature of the mixture is kept below 50° C. Additional toluene is added portion-wise The mixture is stirred at RT overnight, then kept at 60-70° C. for 6 h while more thionyl chloride is added two times (190 mL total). The mixture is cooled and poured in 1 kg ice and 400 mL toluene.

The layers are separated and the organic layer is washed water. The aqueous layers are extracted with toluene. The organic layers are dried and rotary evaporated to yield 485 g of a solidifying oil. $^1$H-NMR (CDCl$_3$): δ 1.4-1.8 (m, 4H), 2.8-3.0 (m, 2H), 3.2-3.9 (m, 8H), 6.3-6.4 (m, 2H).

5,6,7,8-tetramethylenebicyclo[2.2.2]oct-2-ene (3)

The chloride 12 (485 g, 1.606 mol) is dissolved in 150 mL THF. The solution is poured in 1 L DMSO (temperature below 20° C.). Potassium hydroxide (630 g, 9.56 mol) is added (temperatures between 15 and 18° C.) while stirring mechanically. The mixture is stirred for 80 h, two 100 g portions of potassium hydroxide powder being added after 16 and 34 h. The mixture is poured in 1.3 kg ice and 1.5 L tert. butylmethyl ether (MTBE). The mixture is filtered. The layers are separated and the organic layer is washed with water The organic layer is dried, filtered, and rotary evaporated. After workup, the total yield of olefin was 230.28 g (1.476 mol, 73% overall yield from the starting anhydride). $^1$H-NMR (CDCl$_3$): δ 3.85 (dd, 2H), 4.95 (s, 4H), 5.15 (s, 4H), 6.4 (dd, 2H).

6,13-etheno-5,6,7,12,13,14-hexahydropentacene (4)

To a cooled mixture of the olefin obtained above (136.7 g, 0.876 mol), 2-bromochlorobenzene (371.1 g, 1.938 mol), and 3700 mL toluene there is added 800 mL 2.5 N n-butyllithium in hexanes (2.0 mol) at temperatures between −35 and −20° C. The solution is stirred for 1 h allowing the temperature to rise to 12° C. To the resulting suspension there is added 400 mL water. The mixture is filtered and washed with 1500 mL hot toluene, the filtrate layers are separated and the organic layers are rotary evaporated. After most of the solvent has been removed there is added heptane to the remaining suspension. The mixture is stirred and cooled with ice, then filtered, the product being washed with heptane. It weighs 154.54 g (0.502 mol, 57%). $^1$H-NMR (CDCl$_3$): δ 3.6 (s, 8H), 4.3 (dd, 2H), 6.85 (dd, 2H), 7.1 (s, 8H).

6,13-dihydro-6,13-ethenopentacene (5)

A stirred mixture of the hexahydropentacene (221.78 g, 0.720 mol), chloranil (362.6 g, 1.475 mol) and 4 L toluene is kept at reflux for 2½h. The mixture is cooled to about 50° C. and 350 mL 33% sodium hydroxide solution is gradually added. The organic layer is separarted, while the aquous layer is washed with toluene. The combined toluene layers are filtered over aluminium oxide and are rotary evaporated. The residue is stirred with a mixture of 500 mL toluene and heptane. Filtration and washing gives 188.0 g of the product (0.618 mol, 86%). $^1$H-NMR (CDCl$_3$): δ 5.35 (dd, 2H), 7.05 (dd, 2H), 7.4 (m, 4H), 7.75 (m, 8H).

Diels-Alder adduct of
6,13-dihydro-6,13-ethenopentacene and
1,1-dimethoxy-2,3,4,5-tetrachlorocyclopentadiene (7)

A mixture of 1,1-dimethoxy-2,3,4,5-tetrachlorocyclopentadiene (100.5 g, 0.381 mol), the dihydropentacene (100.83 g, 0.332 mol) and 500 mL 1,2,4-trimethylbenzene is heated under reflux for 7 days. NMR indicates that less than 10% of starting olefin is left. The solvent is removed and toluene is added to the residue. The mixture is filtered over an aluminium oxide and silicagel (6×15 cm each) using toluene as the eluent. The eluate is rotary evaporated and the residue is heated with heptane containing some toluene. Cooling, filtration and washing with heptane gives 132.25 g of the product. From residues another 21.29 g of product was isolated. Total yield: 153.54 g (0.270 mol, 81%). $^1$H-NMR (CDCl$_3$): δ 3.35 (s, 2H), 3.55 (s, 3H), 3.65 (s, 3H), 4.65 (s, 2H), 7.3-8.0 (m, 12H).

6,13-dihydro-6,13-(2,3,4,5-tetrachloro-2,4-cyclohexadieno)-pentacene (1)

A mixture of the acetal obtained above (14.1 g, 24.8 mmol), 115 mL toluene, 115 mL heptane, 18 mL water and 120 mL conc. sulphuric acid is heated for 3 days at 65° C., with mechanical stirring. After cooling the liquid is decanted from the solid, washed with water and rotary evaporated. The solid in the flask is diluted with water, sufficient dichloromethane is added to dissolve all product, the mixture is filtered over some Celite, the filtrate layers are separated, the organic layer is; washed with water, dried and rotary evaporated. The residue is stirred with ethyl acetate, then filtered and washed to give 9.09 g of product (18.40 mmol, 74%). $^1$H-NMR (CDCl$_3$): δ 3.50 (s, 2H), 5.10 (s, 2H), 7.45 (m, 4H), 7.8 (m, 8H). The deacetalized intermediate 1 singlets at 3.15 and 4.8 ppm.

The invention claimed is:

1. A method of preparation of a precursor oligocene compound comprising a cyclohexadienyl-group, the precursor oligocene having the formula

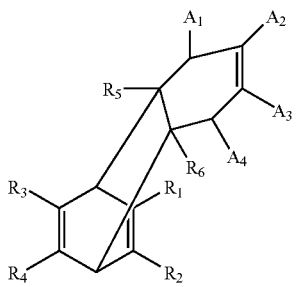

in which:
the cyclohexadienyl-group is optionally provided with a —C(O)-bridge between its 2 and 5 positions;

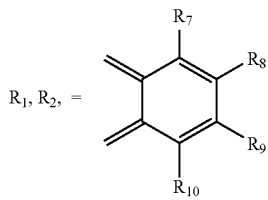

$R_3$, $R_4$ are the same as $R_1$, $R_2$ or are H, alkyl, aryl, alkoxy, aryloxy or halogen
$R_5$, $R_6$ are H, $C_1$-$C_4$-alkyl, CN, $C_1$-$C_4$-alkoxy or halogen and may be the same or different;

$R_7$, $R_8$, $R_9$, $R_{10}$ are H, alkyl, aryl, halogen or alkoxy, and may be the same or different, and $R_7$ and $R_8$, $R_8$ and $R_9$, $R_9$ and $R_{10}$ may be in combination

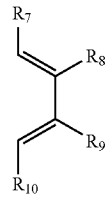

$A_1$, $A_2$, $A_3$, $A_4$, are H or an electron withdrawing group selected from the group consisting of Cl, Br, I, F, H, CN, OCH$_3$, CF$_3$, and may be the same or different,
wherein the method comprises the acts of:
a) reacting a dihydro-etheno-oligocene of the formula

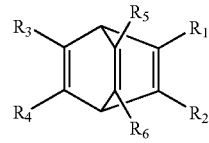

with a 1,1-disubstituted-cyolopentadiene of the formula

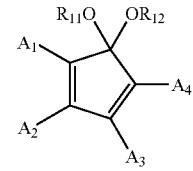

to form a Diels-Alder adduct of the formula

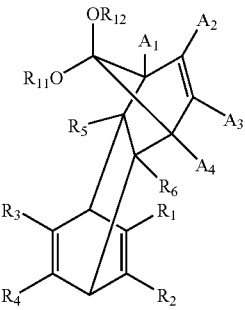

in which
$R_1$-$R_6$ and $A_1$-$A_4$ are the same as above, and
$R_{11}$, $R_{12}$ is H, $C_1$-$C_8$-alkyl, aryl, aralkyl or alkaryl and $R_1$ and $R_2$ may be different or equal to each other, and may form together a ringshaped chain; and
b) converting the adduct with an electrophilic or oxidizing agent to obtain the precursor oligocene compound.

2. The method of claim 1, further comprising the act of converting the precursor oligocene compound to a pentacene of the formula

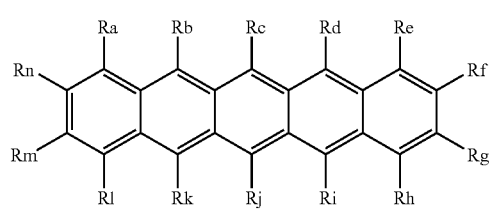

in which $R_a, \ldots, R_n$ are H, alkyl, functionalized alkyl, aryl, alkoxy, and may be the same or different.

3. The method of claim 1, wherein $A_1, A_2, A_3$ and $A_4$ are halogens.

4. The method of claim 1, wherein $A_1, A_2, A_3$ and $A_4$ include Cl.

5. The method of claim 1, wherein $R_{11}$, $R_{12}$ are methyl.

6. The method of claim 1, wherein the dihydro-ethenooligocene of the formula

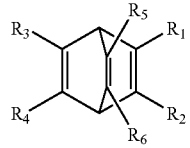

is 6,13-dihydro-6,13-ethenopentacene and is obtained by conversion of bicyclo[2.2.2]oct-2-ene-dianhydride into 5,6,7,8-tetramethylenebicyclo[2.2.2]oct-2ene; and conversion of the tetramethylene-bicyclo-octene with a 1,2-dihalogenobenzene and subsequent reduction.

7. A precursor oligocene compound of the formula

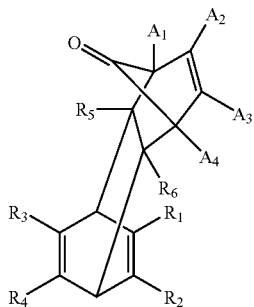

in which

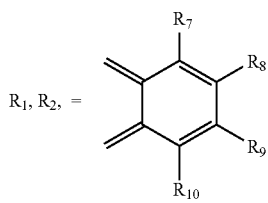

$R_3$, $R_4$ are the same as $R_1$, $R_2$ or are H, alkyl, aryl, alkoxy, aryloxy, or halogen;

$R_5$, $R_6$ are H, $C_1$-$C_4$-alkyl, CN, $C_1$-$C_4$-alkoxy or halogen, and may be the same or different;

$R_7$, $R_8$, $R_9$, $R_{10}$ are H, alkyl, aryl, halogen or alkoxy, and may be the same or different, and $R_7$ and $R_8$, $R_8$ and $R_9$, $R_9$ and $R_{10}$ may be in combination

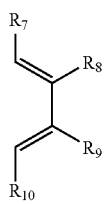

$A_1, A_2, A_3, A_4$, are H or an electron withdrawing group selected from the consisting of Cl, Br, I, F, H, CN, $OCH_3$, $CF_3$, and may be the same or different.

8. An intermediate of the formula

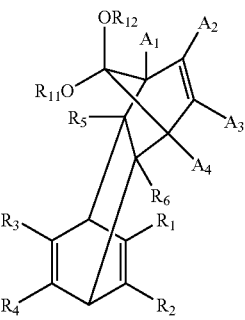

in which

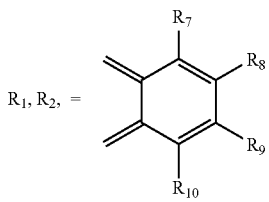

$R_3$, $R_4$ are the same as $R_1$, $R_2$ or are H, alkyl, aryl, alkoxy, aryloxy, or halogen;

$R_5$, $R_6$ are H, $C_1$-$C_4$-alkyl, CN, $C_1$-$C_4$-alkoxy or halogen and may be the same or different;

$R_7$, $R_8$, $R_9$ $R_{10}$ are H, alkyl, aryl, halogen or alkoxy, and may be the same or different, and $R_7$ and $R_8$, $R_8$ and $R_9$, $R_9$ and $R_{10}$ may be in combination

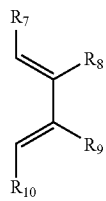

$A_1, A_2, A_3, A_4$, are H or an electron withdrawing group selected from the group consisting of Cl, Br, I, F, H, CN, $OCH_3$, $CF_3$, and may be the same or different; and $R_{11}$, $R_{12}$ are H, $C_1$-$C_8$-alkyl, aryl, aralkyl, or alkaryl, and $R_1$ and $R_2$ may be different or equal to each other, and may form together a ringshaped chain.

9. The method of claim 1, further comprising converting the precursor oligocene compound to the Oligocene at a temperature between 100°C. and 230°C.

* * * * *